(12) United States Patent
Nakamura et al.

(10) Patent No.: US 12,733,883 B2
(45) Date of Patent: Sep. 15, 2026

(54) HEALTH ASSESSMENT SYSTEM, HEALTH ASSESSMENT METHOD, AND STORAGE MEDIUM STORING HEALTH ASSESSMENT PROGRAM

(71) Applicant: HONDA MOTOR CO., LTD., Tokyo (JP)

(72) Inventors: Keisuke Nakamura, Wako (JP); Satoru Shinkawa, Wako (JP); Tomohiro Imai, Wako (JP); Shigenobu Mitsuzawa, Wako (JP); Hideki Sakai, Wako (JP); Hiroshi Ono, Wako (JP); Masahiro Kimura, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 295 days.

(21) Appl. No.: 18/241,296

(22) Filed: Sep. 1, 2023

(65) Prior Publication Data

US 2024/0081749 A1 Mar. 14, 2024

(30) Foreign Application Priority Data

Sep. 14, 2022 (JP) ................................ 2022-146231

(51) Int. Cl.
*A61B 5/00* (2006.01)
*A61B 5/11* (2006.01)

(52) U.S. Cl.
CPC .......... *A61B 5/7285* (2013.01); *A61B 5/1118* (2013.01); *A61B 5/6802* (2013.01); *A61B 5/742* (2013.01)

(58) Field of Classification Search
CPC ... A61B 5/7285; A61B 5/1118; A61B 5/6802; A61B 5/742
See application file for complete search history.

(56) References Cited

U.S. PATENT DOCUMENTS

2017/0265817 A1 9/2017 Takamatsu et al.
2020/0107755 A1 4/2020 Kubo et al.
(Continued)

FOREIGN PATENT DOCUMENTS

JP 2005-045696 A 2/2005
JP 2009-014258 A 1/2009
(Continued)

OTHER PUBLICATIONS

Japanese Office Action dated Sep. 2, 2025 issued in corresponding Japanese application No. 2022-146231; English translation included (8 pages).
(Continued)

*Primary Examiner* — Amanda L Steinberg
(74) *Attorney, Agent, or Firm* — Rankin, Hill & Clark LLP

(57) ABSTRACT

A health assessment system includes a processor that acquires biometric measurement data measured by a wearable terminal worn by a target person, the biometric measurement data being biometric data of the target person; generates complementary biometric data for complementing the biometric measurement data in a missing period in which the acquisition unit is not able to acquire the biometric measurement data from the wearable terminal; and assesses a health condition of the target person based on the biometric measurement data and the complementary biometric data, the processor acquires exercise information, which is information about exercise of the target person, from a mobile terminal carried by the target person, generates the complementary biometric data in the missing period, based on the exercise information of the target person which is obtained from the mobile terminal.

7 Claims, 4 Drawing Sheets

(56) References Cited

U.S. PATENT DOCUMENTS

| | | | | |
|---|---|---|---|---|
| 2020/0367816 | A1* | 11/2020 | Panneer Selvam .. | A61B 5/7475 |
| 2022/0079530 | A1* | 3/2022 | Capodilupo ....... | A61B 5/02055 |
| 2023/0139218 | A1* | 5/2023 | Fukushi ................. | G16H 50/20 702/19 |
| 2023/0301560 | A1 | 9/2023 | Dajani et al. | |
| 2024/0127963 | A1 | 4/2024 | Fukushi et al. | |
| 2024/0127964 | A1 | 4/2024 | Fukushi et al. | |
| 2024/0127965 | A1 | 4/2024 | Fukushi et al. | |

FOREIGN PATENT DOCUMENTS

| | | | |
|---|---|---|---|
| JP | 2016-110317 | A | 6/2016 |
| JP | 2017-221551 | A | 12/2017 |
| JP | 2018-200638 | A | 12/2018 |
| JP | 2019-30596 | A | 2/2019 |
| JP | 2019-180666 | A | 10/2019 |
| JP | 6969831 | B1 | 11/2021 |
| WO | 2021/210172 | A1 | 10/2021 |
| WO | 2022/117713 | A1 | 6/2022 |

OTHER PUBLICATIONS

Japanese Office Action dated Dec. 16, 2025 issued in corresponding Japanese application No. 2022-146231; English machine translation included (9 pages).

Japanese Office Action dated Apr. 28, 2026 issued in corresponding Japanese application No. 2022-146231; English machine translation included (7 pages).

* cited by examiner

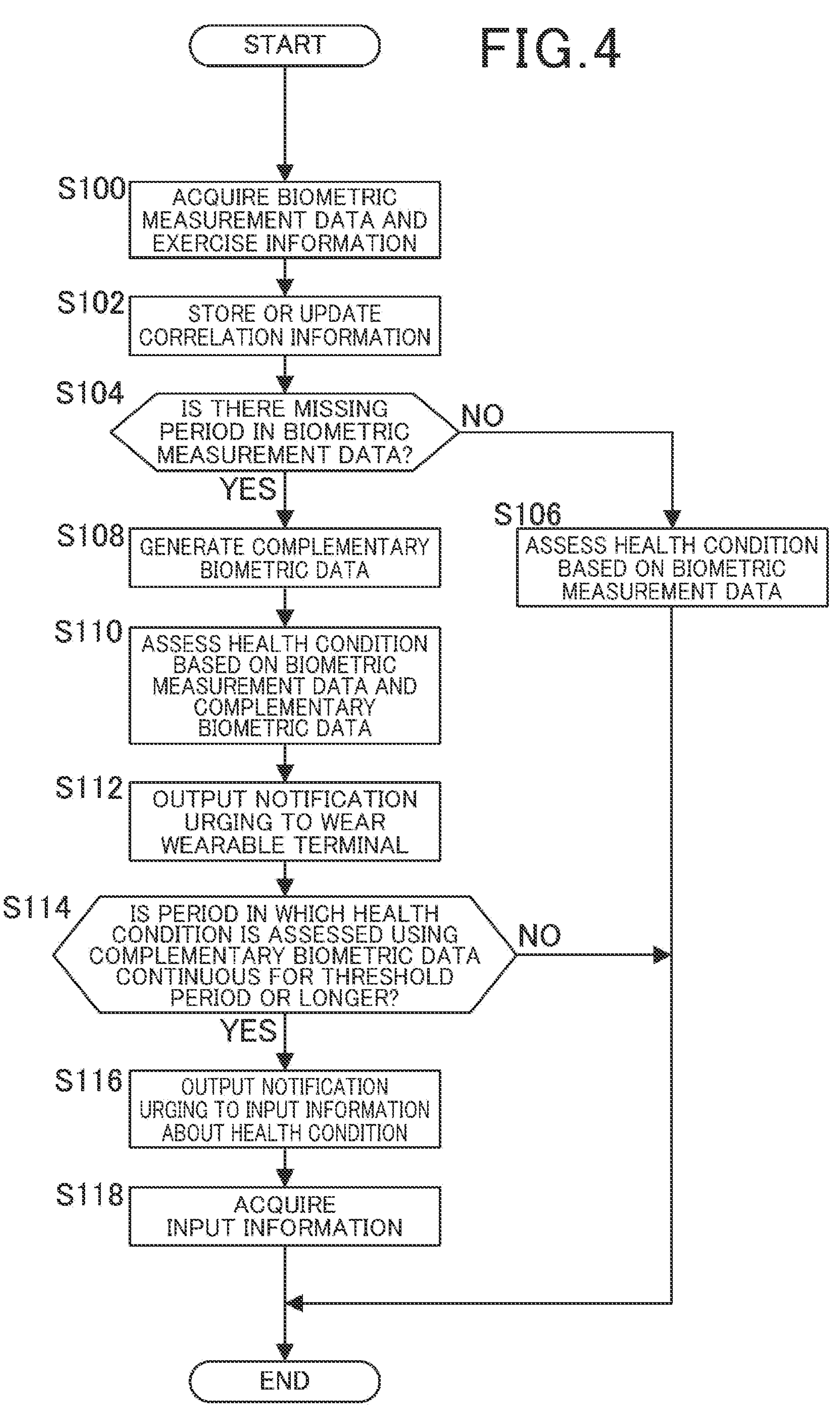
FIG.4
START
S100
ACQUIRE BIOMETRIC MEASUREMENT DATA AND EXERCISE INFORMATION
S102
STORE OR UPDATE CORRELATION INFORMATION
S104
IS THERE MISSING PERIOD IN BIOMETRIC MEASUREMENT DATA?
NO
YES
S106
ASSESS HEALTH CONDITION BASED ON BIOMETRIC MEASUREMENT DATA
S108
GENERATE COMPLEMENTARY BIOMETRIC DATA
S110
ASSESS HEALTH CONDITION BASED ON BIOMETRIC MEASUREMENT DATA AND COMPLEMENTARY BIOMETRIC DATA
S112
OUTPUT NOTIFICATION URGING TO WEAR WEARABLE TERMINAL
S114
IS PERIOD IN WHICH HEALTH CONDITION IS ASSESSED USING COMPLEMENTARY BIOMETRIC DATA CONTINUOUS FOR THRESHOLD PERIOD OR LONGER?
NO
YES
S116
OUTPUT NOTIFICATION URGING TO INPUT INFORMATION ABOUT HEALTH CONDITION
S118
ACQUIRE INPUT INFORMATION
END

HEALTH ASSESSMENT SYSTEM, HEALTH ASSESSMENT METHOD, AND STORAGE MEDIUM STORING HEALTH ASSESSMENT PROGRAM

INCORPORATION BY REFERENCE

The present application claims priority under 35 U.S.C. § 119 to Japanese Patent Application No. 2022-146231 filed on Sep. 14, 2022. The content of the application is incorporated herein by reference in its entirety.

BACKGROUND OF THE INVENTION

Field of the Invention

The present invention relates to a health assessment system, a health assessment method, and a storage medium storing a health assessment program.

Description of the Related Art

A mobile electronic device is disclosed in Japanese Patent Laid-Open No. 2009-14258 that outputs an optimal walking tempo for pedestrians. Such a mobile electronic device detects a heart rate and a walking tempo, and selects and outputs a tempo slower than the detected walking tempo from stored walking tempos when the detected heart rate is equal to or higher than a stored highest heart rate.

A program is disclosed in Japanese Patent Laid-Open No. 2019-180666 that causes a server and a smartphone capable of detecting pulse waves to cooperate with each other to analyze mental aspects of a user of the smartphone. The program causes the smartphone to perform processes of: capturing an image of a fingertip of a user, who refers to the content, with a camera mounted on the smartphone; and transmitting data, in which a fingertip video luminance signal, information on the content, and a pulse wave detection time are associated with each other, to a server, and causes the server to perform the aforementioned analysis.

A health information management method is disclosed in Japanese Patent Laid-Open No. 2005-45696 that includes storing and accumulating health information input using a mobile terminal from a user, creating a health-related rule by analyzing a tendency of a change in physical condition of each user from such health information, and transmitting the health-related rule to the user's mobile terminal every time the user inputs the health-related information.

In order to correctly determine a health condition of a person, it is desirable to use biometric data measured continuously or temporally uninterruptedly. As a device capable of measuring temporally uninterruptedly, a wearable terminal such as a smart watch can be used that can be worn on a person's body. However, for example, it is not necessarily easy to constantly wear a wearable terminal such as a wristwatch having relatively less comfort of wearing, depending on persons or various situations in daily life, and there may be periods in which the person does not wear the wearable terminal. Such a period becomes a period in which biometric data cannot be measured (hereinafter, referred to as a missing period), and may cause an error or a mistake in determination of a health condition based on biometric data.

An object of the present invention is to appropriately assess a health condition even when there is a missing period during continuous measurement of biometric data of a target person with a wearable terminal.

SUMMARY OF THE INVENTION

An aspect of the present invention provides a health assessment system including: an acquisition unit that acquires biometric measurement data measured by a wearable terminal worn by a target person, the biometric measurement data being biometric data of the target person; a complementation unit that generates complementary biometric data for complementing the biometric measurement data in a missing period in which the acquisition unit is not able to acquire the biometric measurement data from the wearable terminal; and an assessment unit that assesses a health condition of the target person based on the biometric measurement data and the complementary biometric data, the acquisition unit being configured to acquire exercise information, which is information about exercise of the target person, from a mobile terminal carried by the target person, the complementation unit being configured to generate the complementary biometric data in the missing period, based on the exercise information of the target person which is obtained from the mobile terminal.

In the health assessment system according to another aspect of the invention, the exercise information obtained from the mobile terminal includes acceleration data and/or positioning data measured by the mobile terminal at predetermined time intervals.

In the health assessment system according to another aspect of the invention, the health assessment system further includes a recording unit that generates correlation information indicating a relationship between a predetermined exercise parameter calculated from the exercise information and a biometric data value based on the biometric measurement data and the exercise information acquired from the mobile terminal when the biometric measurement data is acquired, and causes a storage device to store the correlation information, and the complementation unit calculates the exercise parameter from the exercise information acquired from the mobile terminal in the missing period, and calculates a biometric data value in the missing period based on the calculated exercise parameter and the correlation information, thereby generating the complementary biometric data.

In the health assessment system according to another aspect of the invention, the health assessment system further includes a notification unit that outputs a notification to the mobile terminal, and the assessment unit instructs the notification unit to output a notification, which urges the target person to wear the wearable terminal, to the mobile terminal when assessing the health condition using the complementary biometric data.

In the health assessment system according to another aspect of the invention, the mobile terminal includes a measurement data unit that acquires biometric measurement data from the wearable terminal at predetermined time intervals, and the measurement data unit outputs a notification, which urges the target person to wear the wearable terminal, to the mobile terminal when not being able to acquire the biometric measurement data from the wearable terminal for a predetermined threshold time or longer.

In the health assessment system according to another aspect of the invention, the health assessment system further includes a notification unit that outputs a notification to the mobile terminal, and the assessment unit instructs the notification unit to output a notification, which urges input of information about the health condition, to the mobile terminal when a period in which the biometric measurement data is complemented with the complementary biometric data to assess the health condition is continuous for a predetermined threshold period or longer.

Another aspect of the present invention provides a health assessment method executed by a computer, the health assessment method including: an acquisition step of acquiring biometric measurement data measured by a wearable terminal worn by a target person, the biometric measurement data being biometric data of the target person; a complementation step of generating complementary biometric data for complementing the biometric measurement data in a missing period in which the biometric measurement data is not able to be acquired from the wearable terminal; and an assessment step of assessing a health condition of the target person based on the biometric measurement data and the complementary biometric data, the acquisition step further including acquiring exercise information, which is information about exercise of the target person, from a mobile terminal carried by the target person, the complementation step including generating the complementary biometric data in the missing period, based on the exercise information of the target person which is obtained from the mobile terminal.

Another aspect of the present invention provides a health assessment program causing a computer of a health assessment system to function as: an acquisition unit that acquires biometric measurement data measured by a wearable terminal worn by a target person, the biometric measurement data being biometric data of the target person; a complementation unit that generates complementary biometric data for complementing the biometric measurement data in a missing period in which the acquisition unit is not able to acquire the biometric measurement data from the wearable terminal; and an assessment unit that assesses a health condition of the target person based on the biometric measurement data and the complementary biometric data, the acquisition unit being configured to acquire exercise information, which is information about exercise of the target person, from a mobile terminal carried by the target person, the complementation unit being configured to generate the complementary biometric data in the missing period, based on the exercise information of the target person which is obtained from the mobile terminal.

According to the aspects of the present invention, even when there is a missing period during continuous measurement of biometric data of a target person with a wearable terminal, it is possible to appropriately complement the biometric data in the missing period and to appropriately assess a health condition.

BRIEF DESCRIPTION OF THE DRAWINGS

FIG. 4 is a flowchart showing a procedure of processing of a health assessment method executed by the health assessment system.

DETAILED DESCRIPTION OF THE PREFERRED EMBODIMENTS

Embodiments of the present invention will be described below with reference to the drawings.

Figure 1:
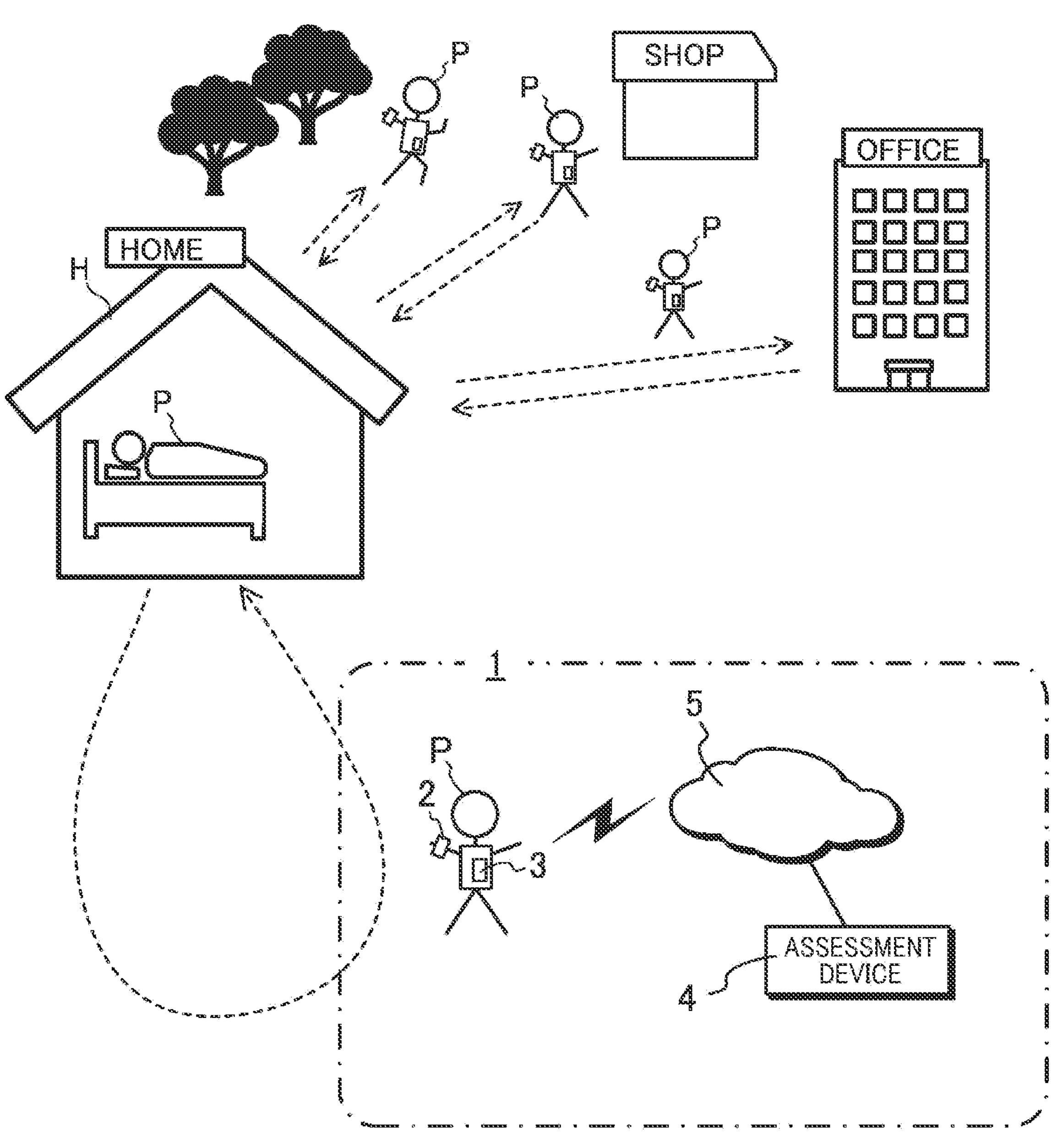
FIG. 1 is a diagram showing a configuration of a health assessment system according to an embodiment of the present invention.

FIG. 1 is a diagram for explaining a configuration of a health assessment system 1 according to an embodiment of the present invention together with an example of its use scene. The health assessment system 1 continuously acquires biometric data of a target person P, and assesses a health condition of the target person P.

The health assessment system 1 includes a wearable terminal 2 and a mobile terminal 3 used by the target person P, and an assessment device 4. By short-range communication such as Bluetooth (registered trademark), the wearable terminal 2 and the mobile terminal 3 are communicably connected to each other. Further, the mobile terminal 3 and the assessment device 4 are communicably connected to each other via a communication network 5 such as the Internet.

The mobile terminal 3 is, for example, a smartphone, and includes an acceleration sensor, a GNSS (Global Navigation Satellite System) sensor, and the like. The wearable terminal 2 is, for example, a wristwatch terminal device, and includes various sensors of a pulse wave sensor, a heart rate sensor, a blood pressure sensor, an acceleration sensor, and/or a GNSS sensor, for example, according to the related art, thereby measuring biometric data of the target person P and transmitting the measured biometric data (hereinafter, also referred to as biometric measurement data) to the mobile terminal 3.

It should be understood that, in FIG. 1, the display of a plurality of target persons P shows the same target person P in various activity scenes. The wearable terminal 2 is worn on the arm of the target person P during all or most of the day, and measures uninterruptedly or chronologically continuously biometric data of the target person P various daily activities including sleeping, eating, and the like at home, exercising (for example, walking, running, and physical training at the gym), shopping, and commuting at predetermined time intervals. The wearable terminal 2 transmits the measured biometric data to the mobile terminal 3, and the mobile terminal 3 receives and acquired such biometric data.

The assessment device 4 acquires biometric measurement data for the target person P from the wearable terminal 2 via the mobile terminal 3. The assessment device 4 also assesses a health condition of the target person P based on the acquired biometric measurement data. In the present embodiment, particularly, where there is a missing period in which the biometric measurement data cannot be acquired from the wearable terminal 2, the assessment device 4 generates complementary biometric data, which complements biometric measurement data in the missing period, based on exercise information of the target person P obtained from the mobile terminal 3 carried by the target person P. Then, the assessment device 4 assesses the health condition of the target person P based on the biometric measurement data and the complementary biometric data.

Thus, according to the health assessment system 1, even when there is a missing period during continuous measurement of the biometric measurement data for the target person P with the wearable terminal 2, the biometric data can be appropriately complemented in the missing period, and the health condition can be appropriately assessed.

Figure 2:
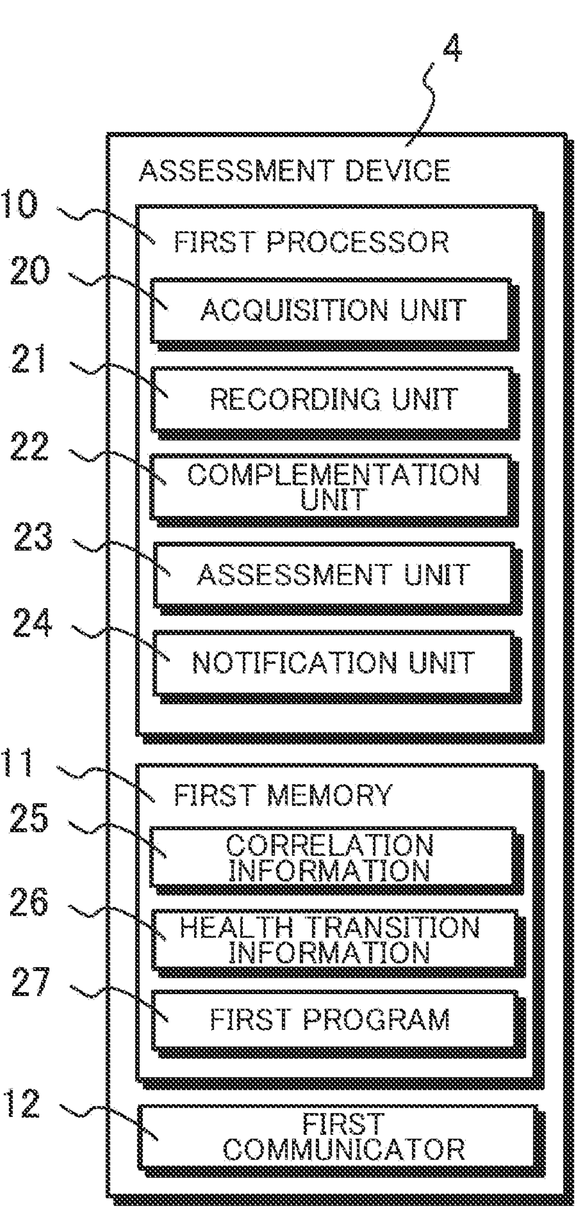
FIG. 2 is a diagram showing a configuration of an assessment device constituting the health assessment system.

FIG. 2 is a diagram showing a configuration of the assessment device 4 constituting the health assessment system 1.

The assessment device 4 includes a first processor 10, a first memory 11, and a first communicator 12. The first memory 11 may be configured by volatile and/or nonvolatile semiconductor memory. The first communicator 12 is a transceiver through which the assessment device 4 communicates with the mobile terminal 3.

The first processor 10 is a computer including a CPU (Central Processing Unit), for example. The first processor 10 may include a ROM (Read Only Memory) in which a program is written, a RAM (Random Access Memory) for temporarily storing data, and the like. Then, the first processor 10 includes an acquisition unit 20, a recording unit 21, a complementation unit 22, an assessment unit 23, and a notification unit 24, as functional components or functional units.

These functional components of the first processor 10 are implemented when the first processor 10 serving as a computer executes a first program 27 stored in the first memory 11. The first program 27 can be stored in any computer-readable storage medium. Alternatively, all or some of the functional components of the first processor 10 may be configured by hardware including one or more electronic circuit components. Here, the first program 27 constitutes a health assessment program in the present disclosure together with a second program 44 executed by the mobile terminal 3.

The acquisition unit 20 acquires the biometric measurement data, which is the biometric data of the target person P measured by the wearable terminal 2 worn by the target person P, via the mobile terminal 3. The acquisition unit 20 also acquires exercise information, which is information about exercise of the target person P, from the mobile terminal 3 carried by the target person P. The exercise information includes, for example, acceleration data indicating acceleration applied to the mobile terminal 3 and position data indicating a position of the mobile terminal 3, which are measured by the mobile terminal 3 at predetermined time intervals. Thus, according to the health assessment system 1, based on the exercise information, it is possible to grasp an exercise state, such as a moving speed or a moving time, of the target person P during the missing period, and to appropriately estimate the biometric data during the missing period.

The recording unit 21 calculates, based on the biometric measurement data acquired from the wearable terminal 2 by the acquisition unit 20 and the exercise information acquired from the mobile terminal 3 when the biometric measurement data is acquired, one or a plurality of pieces of specimen data indicating a relationship between predetermined exercise parameters, which are calculated from the exercise information, and biometric data values, and stores such specimen data in the first memory 11 serving as a storage device, as correlation information 25. The exercise parameters may include, for example, a moving speed, a moving time, and/or the number of steps per predetermined time of the target person P, which are calculated based on time-series data of the acceleration data and/or positioning data obtained from the exercise information. Further, the biometric data values may include a heart rate, a blood flow, a blood pressure value, and/or a sweat rate. The specimen data may be data representing a correlation between the exercise parameters and the biometric data values, such as, for example, the heart rate as the biometric data value becomes ** beats/min. when a person moves at a moving speed of 6 km/h for 10 minutes.

The complementation unit 22 generates complementary biometric data, which is biometric data for complementing the biometric measurement data, during the missing period in which the acquisition unit 20 cannot acquire the biometric measurement data from the wearable terminal 2. In the present embodiment, particularly, the complementation unit 22 generates complementary biometric data, based on the exercise information of the target person P during the missing period, which is obtained from the mobile terminal 3 by the acquisition unit 20. Thus, according to the health assessment system 1, even when there is a missing period during continuous measurement of the biometric measurement data for the target person P with the wearable terminal 2, based on the exercise information, it is possible to grasp an exercise state, such as a moving speed or a moving time, of the target person P during the missing period, and to appropriately generate the complementary biometric data during the missing period.

Specifically, the complementation unit 22 calculates an exercise parameter from the exercise information in the missing period acquired from the mobile terminal 3, calculates a biometric data value in the missing period based on the calculated exercise parameter and the correlation information 25, and generates the complementary biometric data.

Here, the exercise parameter in the missing period can be calculated for each time at predetermined time intervals, for example. The complementation unit 22 calculates a biometric data value such as a heart rate for each time during the missing period, based on the calculated exercise parameter for each time and the correlation information 25 stored in the first memory 11. Then, the complementation unit 22 uses the calculated biometric data value for each time during the missing period, as complementary biometric data.

The assessment unit 23 assesses the health condition of the target person P, based on the biometric measurement data acquired by the acquisition unit 20 and the complementary biometric data generated by the complementation unit 22 (that is, by complementing the biometric measurement data with the complementary biometric data). For example, the assessment unit 23 assesses the health condition at predetermined time intervals (for example, every week), and stores health transition information 26, in which results of the assessment are summarized in time series, in the first memory 11.

In the present embodiment, when assessing the health condition of the target person P using the complementary biometric data, the assessment unit 23 instructs a notification unit 24, which will be described below, to output a notification, which urges the target person P to wear the wearable terminal 2, to the mobile terminal 3. Thus, it is possible to urge the target person P to wear the wearable terminal 2 at an appropriate timing.

When the assessment unit 23 complements the biometric measurement data with the complementary biometric data and continuously evaluates the health condition of the target person P for a predetermined threshold period or longer, the assessment unit 23 may instruct the notification unit 24 to output an input request notification, which is a notification for urging to input information about the health condition, to the mobile terminal 3. For example, when the predetermined threshold period is set to three weeks, the assessment of the health condition performed every week is performed continuously three times or more (that is, continuously for three weeks or more) by complementing the biometric measurement data with the complementary biometric data, and the assessment unit 23 performs the input request notification at this time.

The input request notification may be, for example, a notification of “Is your physical condition the same as usual?” or “Please input your current physical condition with a 5-level evaluation (1—poor to 5—good)”. The mobile terminal 3 displays, for example, the notification as a text message on a touch panel 33 (which will be described below) of the mobile terminal 3 according to the instruction from the notification unit 24.

In response to this, the target person P can input a response on the touch panel 33. The input response is transmitted from the mobile terminal 3 to the assessment device 4, and the assessment unit 23 acquires the response. The assessment unit 23 adds the acquired response to the health transition information 26 and stores it. Thus, according to the health assessment system 1, when the health condition is continuously assessed using the complementary biometric data for a predetermined period or longer, the information about the health condition is acquired from the target person himself/herself, whereby it is possible to prevent an occurrence of cumulative error in the assessment of the health condition, and to make the target person indirectly recognize the importance of wearing of the wearable terminal.

The notification unit 24 causes the mobile terminal 3 to output the notification. For example, the notification unit 24 transmits a text message indicating contents of the notification to be output and an output request to the mobile terminal 3. At this time, when the notification indicates a request of an input from the target person P, the notification unit 24 transmits an input request together with the output request. The mobile terminal 3 displays the text message on the touch panel in response to receiving the output request. In addition, upon receiving the input request, the mobile terminal 3 transmits input information, which is information to be input to the touch panel, to the assessment device 4 after displaying the text message. Then, the notification unit 24 acquires the input information. At this time, the notification unit 24 delivers the acquired input information to the assessment unit 23 when the notification is based on an instruction from the assessment unit 23.

Figure 3:
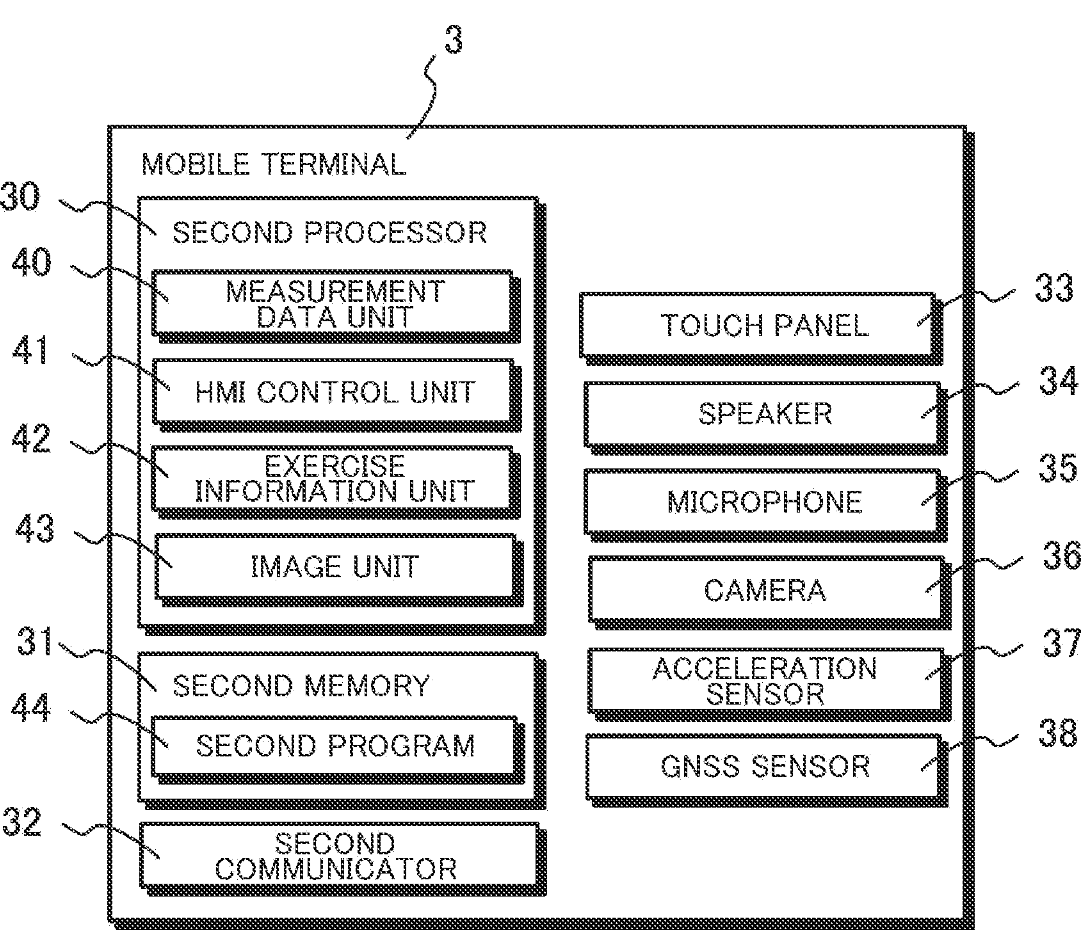
FIG. 3 is a diagram showing a configuration of a mobile terminal constituting the health assessment system.

FIG. 3 is a diagram showing a configuration of the mobile terminal 3 constituting the health assessment system 1.

The mobile terminal 3 includes a second processor 30, a second memory 31, a second communicator 32, a touch panel 33, a speaker 34, a microphone 35, a camera 36, an acceleration sensor 37, and a GNSS sensor 38.

The second memory 31 may be configured by volatile and/or non-volatile semiconductor memory. The second communicator 32 is a transceiver through which the mobile terminal 3 communicates with the wearable terminal 2 and the assessment device 4. For example, the second communicator 32 can include a short-range communicator for performing short-range communication conforming to a Bluetooth communication standard with the wearable terminal 2, and a long-range communicator for communicating with the assessment device 4 via the communication network 5.

The second processor 30 is a computer including a CPU, for example. The second processor 30 may include a ROM in which a program is written, a RAM for temporarily storing data, and the like. The second processor 30 includes a measurement data unit 40, an HMI control unit 41, an exercise information unit 42, and an image unit 43, as functional components or functional units.

These functional components of the second processor 30 are implemented when the second processor 30 serving as a computer executes a second program 44 stored in the second memory 31, for example. The second program 44 can be stored in any computer-readable storage medium. Alternatively, all or some of the functional components of the second processor 30 may be configured by hardware including one or more electronic circuit components. As described above, the second program 44 constitutes a health assessment program in the present disclosure together with the first program 27 executed by the assessment device 4.

The measurement data unit 40 acquires the biometric measurement data of the target person P from the wearable terminal 2 at predetermined time intervals (for example, every minute) via the second communicator 32, and stores the acquired data in the second memory 31. The measurement data unit 40 also transmits the stored biometric measurement data to the assessment device 4 in response to the request from the assessment device 4 or at predetermined time intervals (for example, every day).

Further, when the biometric measurement data cannot be acquired from the wearable terminal 2 for a predetermined threshold time or longer, the measurement data unit 40 instructs the HMI control unit 41, which will be described below, to output a notification, which urges the target person P to wear the wearable terminal 2, to the mobile terminal 3. The notification may be performed by displaying a text message on the touch panel, for example.

Thus, according to the health assessment system 1, it is possible to early urge the target person P to wear the wearable terminal 2, based on a non-wearing time of the wearable terminal 2.

The HMI control unit 41 controls a display operation and an input operation of the touch panel 33. In addition, the HMI control unit 41 controls a sound output to the speaker 34, and processes a voice input from the microphone 35. In the present embodiment, the HMI control unit 41 displays the notification, which urges the target person P to wear the wearable terminal 2, on the touch panel 33 according to the instruction from the measurement data unit 40. Further, the HMI control unit 41 displays the instructed notification on the touch panel 33 according to the instruction from the assessment device 4, acquires information input to the touch panel 33 by the target person P in response to the notification, and transmits the information to the assessment device 4.

The exercise information unit 42 acquires the acceleration applied to the mobile terminal 3 and the position of the mobile terminal 3 at predetermined time intervals (for example, every minute) based on sensor signals from the acceleration sensor 37 and the GNSS sensor 38, and stores time-series data of acceleration data indicating the acceleration and positioning data indicating the position in the second memory, as exercise information. In addition, the exercise information unit 42 transmits the stored exercise information to the assessment device 4 in response to the request from the assessment device 4 or at predetermined time intervals (for example, every day).

The image unit 43 transmits an image, which is captured by the camera 36, to the assessment device 4 according to the instruction from the assessment device 4, for example.

Next, a procedure of the operation in the health assessment system 1 will be described. FIG. 4 is a flowchart showing a procedure of main processes in a health assessment method executed by the health assessment system 1. The processing in FIG. 4 is repeatedly executed at predetermined time intervals. Separately from or in parallel with this processing shown in FIG. 4, it is assumed that each of the measurement data unit 40 and the exercise information unit 42 of the mobile terminal 3 constituting the health assessment system 1 continuously acquires biometric measurement data of the target person P from the wearable terminal 2 at predetermined time intervals, for example, as a part of the health assessment method, and acquires exercise information including acceleration data and positioning data in the mobile terminal 3. Further, separately from or in parallel with this processing shown in FIG. 4, the measurement data unit 40 of the mobile terminal 3 outputs a notification, which urges the target person P to wear the wearable terminal 2, to the mobile terminal 3, when the biometric measurement data cannot be acquired from the wearable terminal 2 for a predetermined time or longer, for example, as a part of the health assessment method.

When the processing shown in FIG. 4 starts, first, the acquisition unit 20 of the assessment device 4 constituting the health assessment system 1 acquires the biometric measurement data and the exercise information of the target person P measured by the wearable terminal 2 from the mobile terminal 3 (S100). Subsequently, the recording unit 21 calculates, based on the biometric measurement data and the exercise information, specimen data indicating a relationship between a predetermined exercise parameter calculated from the exercise information and a biometric data value, and stores such specimen data as the correlation information 25 in the first memory 11 (S102). For example, when the correlation information 25 is already stored in the first memory 11, the recording unit 21 updates the correlation information 25 with the specimen data calculated in advance.

Next, the complementation unit 22 determines whether there is a missing period in the biometric measurement data acquired in step S100 (S104). Then, when there is no missing period (S104, NO), the assessment unit 23 assesses the health condition of the target person P based on the biometric measurement data (S106), and adds the result of the assessment to the health transition information 26 stored in the first memory 11, and this processing ends.

On the other hand, when there is a missing period (S104, YES), the complementation unit 22 generates complementary biometric data in the missing period, based on the exercise information in the missing period included in the exercise information acquired in step S100 and the correlation information 25 (S108).

Next, the assessment unit 23 assesses the health condition of the target person P, based on the biometric measurement data and the complementary biometric data (that is, by complementing biometric measurement data with the complementary biometric data) (S110). The assessment unit 23 adds the result of the assessment to the health transition information 26 stored in the first memory 11.

Subsequently, the assessment unit 23 instructs the notification unit 24 to output a notification, which urges the target person P to wear the wearable terminal 2, to the mobile terminal 3 (S112). In addition, the assessment unit 23 determines whether the period in which the health condition of the target person P is assessed by complementing the biometric measurement data with the complementary biometric data, that is, the period in which the health condition is assessed using the complementary biometric data is continuous for a predetermined period or longer (S114). Then, when the period in which the health condition is assessed using the complementary biometric data is continuous for the predetermined period or longer (S114, YES), the assessment unit 23 instructs the notification unit 24 to output a notification, which urges input of the information about the health condition, to the mobile terminal 3 (S116). The assessment unit 23 acquires a response of the target person P to the notification from the mobile terminal 3, and adds the response to the health transition information 26 (S118), and then this processing ends.

On the other hand, when the assessment unit 23 determines in step S114 that the period in which the health condition is assessed using the complementary biometric data is not continuous for the predetermined period or longer (S114, NO), this processing ends.

In the above, step S100 corresponds to an acquisition step in the present disclosure. Step S108 corresponds to a complementary step in the present disclosure. Further, steps S106 and S110 correspond to assessment steps in the present disclosure.

OTHER EMBODIMENTS

Some of the functional components included in the assessment device 4 of the present embodiment may be provided in another device such as the mobile terminal 3, which is communicably connected to the assessment device 4, in a concentrated or distributed manner. For example, the acquisition unit 20, the recording unit 21, the complementation unit 22, the assessment unit 23, and the notification unit 24 included in the assessment device 4 shown in FIG. 2 may be provided in the mobile terminal 3 in a concentrated manner. In this case, the first program 27 for implementing these functional components is also executed by the mobile terminal 3, and the health assessment system 1 can be implemented only by the mobile terminal 3. In this case, the health assessment program including the first program 27 and the second program 44 can be provided as one application program executed by the mobile terminal 3. Such an application program can be stored in any computer-readable storage medium.

Alternatively, the health assessment system 1 includes an additional server, which is communicably connected to the mobile terminal 3 and the assessment device 4, for information processing, and the acquisition unit 20, the recording unit 21, the complementation unit 22, the assessment unit 23, and/or the notification unit 24 may be implemented in a computer of the additional server. Alternatively, the acquisition unit 20, the recording unit 21, the complementation unit 22, the assessment unit 23, and/or the notification unit 24 may be implemented by being distributed to the mobile terminal 3, the assessment device 4, and the additional server. In such a case, all of the first program 27 executed by the assessment device 4, the second program 44 executed by the mobile terminal 3, and the program executed by the computer of the additional server are equivalent to the health assessment program in the present disclosure.

It should be noted that the present invention is not limited to the configuration of the above-described embodiment, and can be implemented in various forms without departing from the gist of the present invention.

Configurations Supported by Embodiments Described Above

The above-described embodiments support the following configurations.

(Configuration 1) A health assessment system including: an acquisition unit that acquires biometric measurement data measured by a wearable terminal worn by a target person, the biometric measurement data being biometric data of the target person; a complementation unit that generates complementary biometric data for complementing the biometric measurement data in a missing period in which the acquisition unit is not able to acquire the biometric measurement data from the wearable terminal; and an assessment unit that assesses a health condition of the target person based on the biometric measurement data and the complementary biometric data, the acquisition unit being configured to acquire exercise information, which is information about exercise of the target person, from a mobile terminal carried by the target person, the complementation unit being configured to generate the complementary biometric data in the missing period, based on the exercise information of the target person which is obtained from the mobile terminal.

According to the health assessment system of Configuration 1, even when there is a missing period during continuous measurement of the biometric measurement data of the target person with the wearable terminal, it is possible to appropriately complement the biometric data in the missing period and to appropriately assess the health condition.

(Configuration 2) In the health assessment system according to Configuration 1, the exercise information obtained from the mobile terminal includes acceleration data and/or positioning data measured by the mobile terminal at predetermined time intervals.

According to the health assessment system of Configuration 2, based on the exercise information, it is possible to grasp an exercise state, such as a moving speed or a moving time, of the target person during the missing period, and to appropriately estimate the biometric data during the missing period.

(Configuration 3) In the health assessment system according to Configuration 1 or 2, the health assessment system further includes a recording unit that generates correlation information indicating a relationship between a predetermined exercise parameter calculated from the exercise information and a biometric data value based on the biometric measurement data and the exercise information acquired from the mobile terminal when the biometric measurement data is acquired, and causes a storage device to store the correlation information, and the complementation unit calculates the exercise parameter from the exercise information acquired from the mobile terminal in the missing period, and calculates a biometric data value in the missing period based on the calculated exercise parameter and the correlation information, thereby generating the complementary biometric data.

According to the health assessment system of Configuration 3, it is possible to calculate the complementary biometric data with less deviation from reality and with high accuracy, based on the correlation information generated based on the actually measured biometric measurement data and the exercise information acquired simultaneously with the biometric measurement data.

(Configuration 4) In the health assessment system according to any one of Configurations 1 to 3, the health assessment system further includes a notification unit that outputs a notification to the mobile terminal, and the assessment unit instructs the notification unit to output a notification, which urges the target person to wear the wearable terminal, to the mobile terminal when assessing the health condition using the complementary biometric data.

According to the health assessment system of Configuration 4, it is possible to urge the target person to wear the wearable terminal at an appropriate timing.

(Configuration 5) In the health assessment system according to any one of Configurations 1 to 4, the mobile terminal includes a measurement data unit that acquires biometric measurement data from the wearable terminal at predetermined time intervals, and the measurement data unit outputs a notification, which urges the target person to wear the wearable terminal, to the mobile terminal when not being able to acquire the biometric measurement data from the wearable terminal for a predetermined threshold time or longer.

According to the health assessment system of Configuration 5, it is possible to early urge the target person to wear the wearable terminal, based on a non-wearing time of the wearable terminal.

(Configuration 6) In the health assessment system according to any one of Configurations 1 to 5, the health assessment system further includes a notification unit that outputs a notification to the mobile terminal, and the assessment unit instructs the notification unit to output a notification, which urges input of information about the health condition, to the mobile terminal when a period in which the biometric measurement data is complemented with the complementary biometric data to assess the health condition is continuous for a predetermined threshold period or longer.

According to the health assessment system of Configuration 6, when the health condition is continuously assessed using the complementary biometric data for a predetermined period or longer, the information about the health condition is acquired from the target person himself/herself, whereby it is possible to prevent an occurrence of cumulative error in the assessment of the health condition, and to make the target person indirectly recognize the importance of wearing of the wearable terminal.

(Configuration 7) A health assessment method executed by a computer, the health assessment method including: an acquisition step of acquiring biometric measurement data measured by a wearable terminal worn by a target person, the biometric measurement data being biometric data of the target person; a complementation step of generating complementary biometric data for complementing the biometric measurement data in a missing period in which the biometric measurement data is not able to be acquired from the wearable terminal; and an assessment step of assessing a health condition of the target person based on the biometric measurement data and the complementary biometric data, the acquisition step further including acquiring exercise information, which is information about exercise of the target person, from a mobile terminal carried by the target person, the complementation step including generating the complementary biometric data in the missing period, based on the exercise information of the target person which is obtained from the mobile terminal.

According to the health assessment method of Configuration 7, even when there is a missing period during continuous measurement of the biometric measurement data of the target person with the wearable terminal, it is possible to appropriately complement the biometric data in the missing period and to appropriately assess the health condition.

(Configuration 8) A health assessment program causing a computer of a health assessment system to function as: an acquisition unit that acquires biometric measurement data measured by a wearable terminal worn by a target person, the biometric measurement data being biometric data of the target person; a complementation unit that generates complementary biometric data for complementing the biometric measurement data in a missing period in which the acquisition unit is not able to acquire the biometric measurement data from the wearable terminal; and an assessment unit that assesses a health condition of the target person based on the biometric measurement data and the complementary biometric data, the acquisition unit being configured to acquire exercise information, which is information about exercise of the target person, from a mobile terminal carried by the target person, the complementation unit being configured to generate the complementary biometric data in the missing period, based on the exercise information of the target person which is obtained from the mobile terminal.

According to the health assessment program of Configuration 8, it is possible to realize the health assessment system capable of appropriately complementing the biometric data in the missing period and appropriately assessing the health condition even when there is a missing period during continuous measurement of the biometric measurement data of the target person with the wearable terminal.

REFERENCE SIGNS LIST

1 health assessment system
2 wearable terminal
3 mobile terminal
4 assessment device
5 communication network
10 first processor
11 first memory
12 first communicator
20 acquisition unit
21 recording unit
22 complementation unit
23 assessment unit
24 notification unit
25 correlation information
26 health transition information
27 first program
30 second processor
31 second memory
32 second communicator
33 touch panel
34 speaker
35 microphone
36 camera
37 acceleration sensor
38 GNSS sensor
40 measurement data unit
41 HMI control unit
42 exercise information unit
43 image unit
44 second program.

What is claimed is:

1. A health assessment system in which a wearable terminal worn by a target person, a mobile terminal used by the target person, and an assessment device comprising a processor are communicably connected to each other via a communication network, wherein the processor:

acquires biometric measurement data measured by the wearable terminal, the biometric measurement data being biometric data of the target person;

generates complementary biometric data for complementing the biometric measurement data in a missing period in which the biometric measurement data cannot be acquired from the wearable terminal;

assesses a health condition of the target person based on the biometric measurement data and the complementary biometric data, and stores health transition information, in which results of assessment are summarized in time series, in a memory;

acquires exercise information, which is information about exercise of the target person, from the mobile terminal;

generates the complementary biometric data in the missing period, based on the exercise information of the target person which is obtained from the mobile terminal; and when a period in which the biometric measurement data is complemented with the complementary biometric data to assess the health condition is continuous for a predetermined threshold period or longer, displays a text message on a touch panel of the mobile terminal requesting an answer about current health condition of the target person, acquires the answer about the current health condition of the target person inputted to the touch panel, and stores, in the memory, the answer by adding the answer to the health transition information.

2. The health assessment system according to claim 1, wherein the exercise information obtained from the mobile terminal includes acceleration data and/or positioning data measured by the mobile terminal at predetermined time intervals.

3. The health assessment system according to claim 1, wherein the processor further generates correlation information indicating a relationship between a predetermined exercise parameter calculated from the exercise information and a biometric data value based on the biometric measurement data and the exercise information acquired from the mobile terminal when the biometric measurement data is acquired, and causes the memory to store the correlation information, and calculates the exercise parameter from the exercise information acquired from the mobile terminal in the missing period, and calculates a biometric data value in the missing period based on the calculated exercise parameter and the correlation information, thereby generating the complementary biometric data.

4. The health assessment system according to claim 1, wherein the processor further outputs a notification, which urges the target person to wear the wearable terminal, to the mobile terminal when assessing the health condition using the complementary biometric data.

5. The health assessment system according to claim 1, wherein the mobile terminal acquires biometric measurement data from the wearable terminal at predetermined time intervals, and the processor outputs a notification, which urges the target person to wear the wearable terminal, to the mobile terminal when not being able to acquire the biometric measurement data from the wearable terminal for a predetermined threshold time or longer.

6. A health assessment method executed by a computer, wherein the computer communicates with a wearable terminal worn by a target person and a mobile terminal used by the target person via a communication network, the health assessment method comprising:

an acquisition step of acquiring biometric measurement data measured by the wearable terminal, the biometric measurement data being biometric data of the target person;

a complementation step of generating complementary biometric data for complementing the biometric measurement data in a missing period in which the biometric measurement data is not able to be acquired from the wearable terminal; and an assessment step of assessing a health condition of the target person based on the biometric measurement data and the complementary biometric data, and storing health transition information, in which results of assessment are summarized in time series, in a memory, the acquisition step further including acquiring exercise information, which is information about exercise of the target person, from the mobile terminal, the complementation step including generating the complementary biometric data in the missing period, based on the exercise information of the target person which is obtained from the mobile terminal, and when a period in which the biometric measurement data is complemented with the complementary biometric data to assess the health condition is continuous for a predetermined threshold period or longer, displays a text message on a touch panel of the mobile terminal requesting an answer about current health condition of the target person, acquires the answer about the current health condition of the target person inputted to the touch panel, and stores, in the memory, the answer by adding the answer to the health transition information.

7. A non-transitory computer-readable storage medium storing a health assessment program which is executed by a computer of a health assessment system, wherein the health assessment program makes the computer function as:

a communicator that communicates with a wearable terminal worn by a target person and a mobile terminal used by the target person via a communication network;

an acquisition unit that acquires biometric measurement data measured by the wearable terminal, the biometric measurement data being biometric data of the target person;

a complementation unit that generates complementary biometric data for complementing the biometric measurement data in a missing period in which the acquisition unit is not able to acquire the biometric measurement data from the wearable terminal; and an assessment unit that assesses a health condition of the target person based on the biometric measurement data and the complementary biometric data, and stores health transition information, in which results of assessment are summarized in time series, in a memory, the acquisition unit being configured to acquire exercise information, which is information about exercise of the target person, from a mobile terminal carried by the target person, the complementation unit being configured to generate the complementary biometric data in the missing period, based on the exercise information of the target person which is obtained from the mobile terminal, and when a period in which the biometric measurement data is complemented with the complementary biometric data to assess the health condition is continuous for a predetermined threshold period or longer, to display a text message on a touch panel of the mobile terminal requesting an answer about current health condition of the target person, to acquire the answer about the current health condition of the target person inputted to the touch panel, and to store, in the memory, the answer by adding the answer to the health transition information.

* * * * *